(12) United States Patent
Dillon

(10) Patent No.: US 11,766,369 B1
(45) Date of Patent: Sep. 26, 2023

(54) SINGLE USE PROTECTIVE COVER FOR PATIENT TRANSPORT DEVICE

(71) Applicant: Douglas Dillon, Park City, UT (US)

(72) Inventor: Douglas Dillon, Park City, UT (US)

( * ) Notice: Subject to any disclaimer, the term of this patent is extended or adjusted under 35 U.S.C. 154(b) by 0 days.

(21) Appl. No.: 17/491,443

(22) Filed: Sep. 30, 2021

Related U.S. Application Data

(60) Provisional application No. 63/085,691, filed on Sep. 30, 2020.

(51) Int. Cl.
| | | |
|---|---|---|
| *A61G 1/048* | (2006.01) | |
| *A61G 1/04* | (2006.01) | |
| *A61G 1/01* | (2006.01) | |
| *A47C 27/00* | (2006.01) | |
| *A47G 9/02* | (2006.01) | |
| *A61F 7/10* | (2006.01) | |
| *A61F 7/08* | (2006.01) | |

(52) U.S. Cl.
CPC ............ *A61G 1/048* (2013.01); *A47C 27/005* (2013.01); *A47G 9/0246* (2013.01); *A61F 7/10* (2013.01); *A61G 1/01* (2013.01); *A47G 9/0238* (2013.01); *A61F 7/08* (2013.01); *A61G 1/04* (2013.01)

(58) Field of Classification Search
CPC . A61G 1/048; A61G 1/04; A61G 1/01; A47C 27/005; A47C 27/002; A47G 9/0246; A47G 9/0238; A61F 7/08; A61F 7/10; A61F 7/106
USPC ............ 5/600, 424, 425, 482, 484, 502, 663
See application file for complete search history.

(56) References Cited

U.S. PATENT DOCUMENTS

| | | |
|---|---|---|
| 1,959,920 A | 6/1933 | Holder |
| 2,602,302 A | 7/1952 | Poux |
| 2,641,779 A | 6/1953 | Gill |
| 2,695,415 A | 11/1954 | Holton |
| 2,810,921 A | 10/1957 | Seidenberg |
| 2,870,464 A | 1/1959 | Lalick |
| 3,060,932 A | 10/1962 | Pereny et al. |
| 3,258,789 A | 7/1966 | Banks |
| 3,290,703 A | 12/1966 | Worrall |
| 3,576,039 A | 4/1971 | Roberts |
| 3,638,251 A | 2/1972 | Weiss |
| 3,654,646 A | 4/1972 | McMahon, Jr. |
| 3,742,530 A | 7/1973 | Clark |
| 3,775,784 A | 12/1973 | Fry |
| 3,824,640 A | 7/1974 | Golden |
| 3,856,006 A | 12/1974 | Krzewinski |
| 3,906,559 A | 9/1975 | Bahr |
| 3,956,782 A | 5/1976 | Morrison |

(Continued)

FOREIGN PATENT DOCUMENTS

| | | |
|---|---|---|
| EP | 0634125 | 1/1995 |
| EP | 2962671 | 1/2016 |

(Continued)

*Primary Examiner* — Robert G Santos
(74) *Attorney, Agent, or Firm* — Clayton Howarth, P.C.

(57) ABSTRACT

A single-use protective cover for patient transport devices is disclosed. Said protective cover is fitted to the patient transport device and can integrate a Mylar® layer to help maintain a patient's body temperature. Additionally an outer layer can be incorporated into the protective cover to enclose the patient and provide another barrier to contain fluids. Said layer can also incorporate active heating or active cooling pads and seat belt covers to prevent contamination of the patient transport device.

52 Claims, 5 Drawing Sheets

(56) References Cited

U.S. PATENT DOCUMENTS

| | | | |
|---|---|---|---|
| 4,026,299 A | 5/1977 | Sauder | |
| 4,040,418 A | 8/1977 | Collins | |
| 4,081,868 A | 4/1978 | Hull | |
| 4,164,941 A | 8/1979 | Knopick et al. | |
| 4,370,765 A | 2/1983 | Webber | |
| 4,384,573 A | 5/1983 | Elliott | |
| 4,461,048 A | 7/1984 | Allaire, Jr. | |
| 4,495,233 A | 1/1985 | Bassetti | |
| D280,573 S | 9/1985 | Barton | |
| 4,553,785 A | 11/1985 | Duke, Jr. et al. | |
| 4,572,174 A | 2/1986 | Eilender et al. | |
| 4,572,188 A | 2/1986 | Augustine et al. | |
| 4,575,097 A | 3/1986 | Brannigan et al. | |
| 4,634,618 A | 1/1987 | Greer et al. | |
| 4,693,691 A | 9/1987 | DeYoe | |
| 4,698,862 A | 10/1987 | Mairs | |
| 4,736,088 A | 4/1988 | Bart | |
| 4,736,762 A | 4/1988 | Wayman | |
| 4,753,241 A | 6/1988 | Brannigan et al. | |
| 4,765,323 A | 8/1988 | Poettgen | |
| 4,807,644 A | 2/1989 | Sandhaus | |
| 4,827,545 A | 5/1989 | Arp | |
| 4,877,288 A | 10/1989 | Lee | |
| 4,886,063 A | 12/1989 | Crews | |
| 4,889,135 A | 12/1989 | Poettgen | |
| 4,892,353 A | 1/1990 | Goddard | |
| 4,895,171 A | 1/1990 | Onik | |
| 4,903,360 A | 2/1990 | Friedman | |
| 4,905,712 A | 3/1990 | Bowlin et al. | |
| 4,924,543 A | 5/1990 | Toss et al. | |
| 4,939,803 A | 7/1990 | Waters | |
| 4,941,222 A | 7/1990 | Prager | |
| 4,945,924 A | 8/1990 | Poettgen | |
| 4,962,761 A | 10/1990 | Golden | |
| 4,979,520 A | 12/1990 | Boone, Jr. et al. | |
| 4,993,092 A * | 2/1991 | Weeks | A61G 1/01 |
| | | | D24/190 |
| 5,003,655 A | 4/1991 | Kafai | |
| 5,020,177 A | 6/1991 | Etherington | |
| 5,025,777 A | 6/1991 | Hardwick | |
| 5,027,456 A | 7/1991 | Wadsworth | |
| 5,044,025 A | 9/1991 | Hunsinger et al. | |
| 5,044,031 A | 9/1991 | Sherwood et al. | |
| 5,070,520 A | 12/1991 | Brown | |
| 5,084,927 A | 2/1992 | Parkevich | |
| 5,088,137 A | 2/1992 | Rose | |
| 5,092,010 A | 3/1992 | Wong | |
| 5,099,530 A | 3/1992 | Scott | |
| 5,118,553 A | 6/1992 | Boisson | |
| 5,125,238 A | 6/1992 | Ragan et al. | |
| 5,146,641 A | 9/1992 | Zwickey | |
| 5,175,897 A | 1/1993 | Marra, Jr. | |
| 5,179,746 A | 1/1993 | Rogers | |
| 5,184,612 A | 2/1993 | Augustine | |
| 5,189,744 A | 3/1993 | Roberts | |
| 5,189,746 A | 3/1993 | Horie | |
| 5,190,032 A | 3/1993 | Zacoi | |
| 5,199,120 A | 4/1993 | Holmes | |
| 5,226,815 A | 7/1993 | Bowman | |
| 5,227,218 A | 7/1993 | Herum | |
| 5,246,656 A | 9/1993 | Stephenson et al. | |
| 5,265,599 A | 11/1993 | Stephenseon et al. | |
| 5,300,098 A | 4/1994 | Philipot | |
| 5,300,103 A | 4/1994 | Stempel et al. | |
| 5,304,213 A | 4/1994 | Berke et al. | |
| 5,324,320 A | 6/1994 | Augustine et al. | |
| 5,345,627 A | 9/1994 | Cammarata | |
| 5,350,417 A | 9/1994 | Augustine | |
| 5,360,439 A | 11/1994 | Dickerhoff et al. | |
| 5,392,847 A | 2/1995 | Stephenson | |
| 5,405,371 A | 4/1995 | Augustine et al. | |
| 5,421,046 A | 6/1995 | Vande Streek | |
| 5,425,975 A | 6/1995 | Koiso et al. | |
| 5,443,488 A | 8/1995 | Namenye et al. | |
| 5,450,641 A | 9/1995 | Montgomery | |
| 5,465,440 A | 11/1995 | Heptner | |
| 5,481,772 A | 1/1996 | Glynn et al. | |
| 5,511,259 A | 4/1996 | Tarara | |
| 5,513,655 A | 5/1996 | Peimer et al. | |
| 5,522,871 A | 6/1996 | Sternlicht | |
| 5,545,194 A | 8/1996 | Augustine | |
| 5,557,817 A | 9/1996 | Haddock | |
| 5,575,025 A | 11/1996 | Peters | |
| 5,579,547 A | 12/1996 | Hunt | |
| 5,615,425 A * | 4/1997 | Corente | A47G 9/0246 |
| | | | 297/229 |
| 5,634,222 A | 6/1997 | Zwickey | |
| 5,642,543 A | 7/1997 | Huntley | |
| 5,644,807 A | 7/1997 | Battistella | |
| D382,164 S | 8/1997 | Hays | |
| 5,669,089 A | 9/1997 | Dees | |
| 5,675,851 A | 10/1997 | Feathers | |
| 5,699,568 A | 12/1997 | Couldridge | |
| 5,713,089 A | 2/1998 | Ferrante | |
| 5,749,112 A | 5/1998 | Metzler | |
| 5,784,730 A | 7/1998 | Hunt | |
| 5,785,219 A | 7/1998 | Kraft | |
| 5,800,483 A * | 9/1998 | Vought | A61F 7/00 |
| | | | 128/853 |
| 5,813,407 A | 9/1998 | Busch | |
| 5,819,339 A | 10/1998 | Hodgetts | |
| 5,819,746 A | 10/1998 | Walton | |
| 5,911,654 A * | 6/1999 | Webb | A47C 31/105 |
| | | | 5/663 |
| 5,950,261 A | 9/1999 | Hay et al. | |
| 5,950,625 A | 9/1999 | Bongiovanni et al. | |
| 5,950,627 A | 9/1999 | Bologovsky et al. | |
| 5,974,606 A | 11/1999 | Moberly | |
| 5,978,989 A | 11/1999 | Chavez | |
| 5,991,666 A * | 11/1999 | Vought | A61B 46/00 |
| | | | 607/104 |
| 6,014,935 A | 1/2000 | Willett | |
| 6,082,535 A | 7/2000 | Mitchell | |
| 6,105,188 A | 8/2000 | Perez-Mesa et al. | |
| 6,122,783 A | 9/2000 | Herndon et al. | |
| 6,128,796 A * | 10/2000 | McCormick | A61G 1/01 |
| | | | 5/663 |
| 6,170,486 B1 | 1/2001 | Islava | |
| 6,182,309 B1 | 2/2001 | Sullivan | |
| 6,199,232 B1 | 3/2001 | Kocivar | |
| 6,418,932 B2 | 7/2002 | Paschal, Jr. et al. | |
| 6,453,492 B1 * | 9/2002 | Sturrock | A47G 9/0238 |
| | | | 5/482 |
| 6,481,736 B1 | 11/2002 | Chan | |
| 6,484,335 B1 | 11/2002 | Gilbert | |
| 6,627,032 B1 | 9/2003 | Chester et al. | |
| 6,673,628 B2 | 1/2004 | Freitag et al. | |
| 6,742,635 B2 | 6/2004 | Hirshberg | |
| 6,899,662 B2 | 5/2005 | Gamble et al. | |
| 6,969,346 B2 | 11/2005 | Perlatti | |
| 7,086,106 B1 * | 8/2006 | Hairston | A47C 21/08 |
| | | | 5/663 |
| 7,100,226 B1 | 9/2006 | Walton | |
| 7,131,156 B1 | 11/2006 | Walker-Craft | |
| 7,222,705 B1 | 5/2007 | Guza | |
| 7,458,117 B2 | 12/2008 | Schaefer | |
| 7,484,275 B2 | 2/2009 | Carroll et al. | |
| 7,503,890 B2 | 3/2009 | Kubiesko et al. | |
| 7,614,105 B1 | 11/2009 | Jackson et al. | |
| 7,678,092 B2 | 3/2010 | Matloub et al. | |
| 7,766,950 B2 | 8/2010 | Castellani et al. | |
| 8,011,371 B2 | 9/2011 | Rotolo | |
| 8,141,555 B1 * | 3/2012 | Neusch | A61G 1/01 |
| | | | 128/869 |
| 8,276,223 B1 | 10/2012 | Connor | |
| 8,464,379 B1 | 6/2013 | Zajac | |
| 9,029,353 B2 | 5/2015 | Baker et al. | |
| D746,386 S | 12/2015 | Mahoney et al. | |
| 9,756,882 B2 | 9/2017 | Townsend | |
| D817,033 S | 5/2018 | Christmas | |
| 10,307,312 B2 * | 6/2019 | Butterfield | A61G 1/048 |
| 2004/0003469 A1 | 1/2004 | Gill-Barajas | |
| 2004/0084053 A1 | 5/2004 | Hess | |

(56) References Cited

U.S. PATENT DOCUMENTS

| | | |
|---|---|---|
| 2005/0028277 A1 | 2/2005 | Gordon et al. |
| 2005/0051203 A1 | 3/2005 | McCully et al. |
| 2005/0198736 A1 | 9/2005 | Jahrling |
| 2006/0021141 A1 | 2/2006 | Shima |
| 2006/0230535 A1 | 10/2006 | Cox |
| 2007/0028382 A1 | 2/2007 | Field et al. |
| 2007/0056096 A1 | 3/2007 | Assink |
| 2007/0151029 A1 | 7/2007 | Bridges |
| 2007/0157935 A1 | 7/2007 | Reynolds |
| 2008/0006279 A1 | 1/2008 | Bodenham et al. |
| 2008/0210245 A1 | 9/2008 | Ricketts |
| 2008/0283164 A1 | 11/2008 | Noonan |
| 2010/0154122 A1 | 6/2010 | Crispino et al. |
| 2010/0186165 A1 | 7/2010 | Marciano |
| 2011/0030140 A1 | 2/2011 | Ruiz |
| 2012/0284916 A1 | 11/2012 | Hill |
| 2013/0014769 A1 | 1/2013 | Christmas |
| 2014/0026895 A1 | 1/2014 | Hodges et al. |
| 2014/0059765 A1 | 3/2014 | Harris |
| 2015/0216745 A1 | 8/2015 | Christmas |
| 2016/0120713 A1* | 5/2016 | Magbee .......... A61G 1/04 5/494 |
| 2016/0220428 A1 | 8/2016 | Butterfield et al. |
| 2017/0145711 A1 | 5/2017 | Esses et al. |

FOREIGN PATENT DOCUMENTS

| | | |
|---|---|---|
| FR | 2699070 | 6/1994 |
| FR | 2847157 | 5/2004 |
| GB | 468336 | 7/1937 |
| WO | WO8503216 | 8/1985 |
| WO | WO9107625 | 5/1991 |
| WO | WO2012138796 | 10/2012 |

* cited by examiner

SINGLE USE PROTECTIVE COVER FOR PATIENT TRANSPORT DEVICE

CROSS-REFERENCE TO RELATED APPLICATIONS

This application claims the benefit of provisional application No. 63/085,691 for Single Use Protective Cover for Patient Transport Device, filed Sep. 30, 2020, which is hereby incorporated by reference herein in its entirety, including but not limited to those portions that specifically appear hereinafter, this incorporation by reference being made with the following exception: In the event that any portion of the above-referenced provisional application is inconsistent with this application, this application supersedes said above-referenced provisional application.

STATEMENT REGARDING FEDERALLY SPONSORED RESEARCH OR DEVELOPMENT

Not Applicable.

BACKGROUND

1. The Field of the Present Disclosure

The present disclosure relates generally to covers used as a protective layer on patient transport devices, such as gurneys and stretchers. More particularly, the present disclosure relates to a cover adapted to serve not only as a protective layer but also to provide other advantages to the patient and health care providers.

2. Description of Related Art

Various devices have been used to transport patients from one location to another. These devices are used in a variety of circumstances, such as within a hospital, or for transportation to, within, and from an emergency vehicle such as an ambulance or helicopter. These devices often have a number of handles, handholds, and attachments creating an odd shape. Such devices often have a mattress-like portion for the patient being transported to rest on. Some type of bedding might be provided, designed to prevent contamination of the mattress area and protect the patient from cross-contamination. However, the shape of the patient transport device, along with the handles, attachments, and perhaps seat belts (for ambulance transport) can create an undesirable situation where a protective barrier in the shape of an ordinary sheet will not cover the entire area of the device where a patient may have contact, such as the handles and seat belts, which leads to the possibility of contamination of the device and cross-contamination with future patients transported by the device.

There have been a variety of types of bedding used for these devices, many of which are now disposable so as to provide a clean device and prevent cross-contamination and infection for subsequent patients. However, customization of covers for patient transport devices have not always kept pace with devices themselves. In addition, the covers for the patient transport devices have been created with the end of serving merely as a barrier between the patient and the device. However, it is unrecognized in the art that a cover can advantageously serve many more functions in accordance with the needs of a patient and the needs of health care providers.

In view of the disadvantages and unrecognized needs present in the already available devices, what is needed is a cover which serves to prevent contamination, and also serves other purposes for the patient and health care providers, depending on the needs of the patient and the providers. Below, disclosure is provided for a single use protective cover for patient transport device which is specifically fitted to a number of patient transport devices to better prevent contamination, and which also provides additional benefits to individual patients being transported and health care providers using said device.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
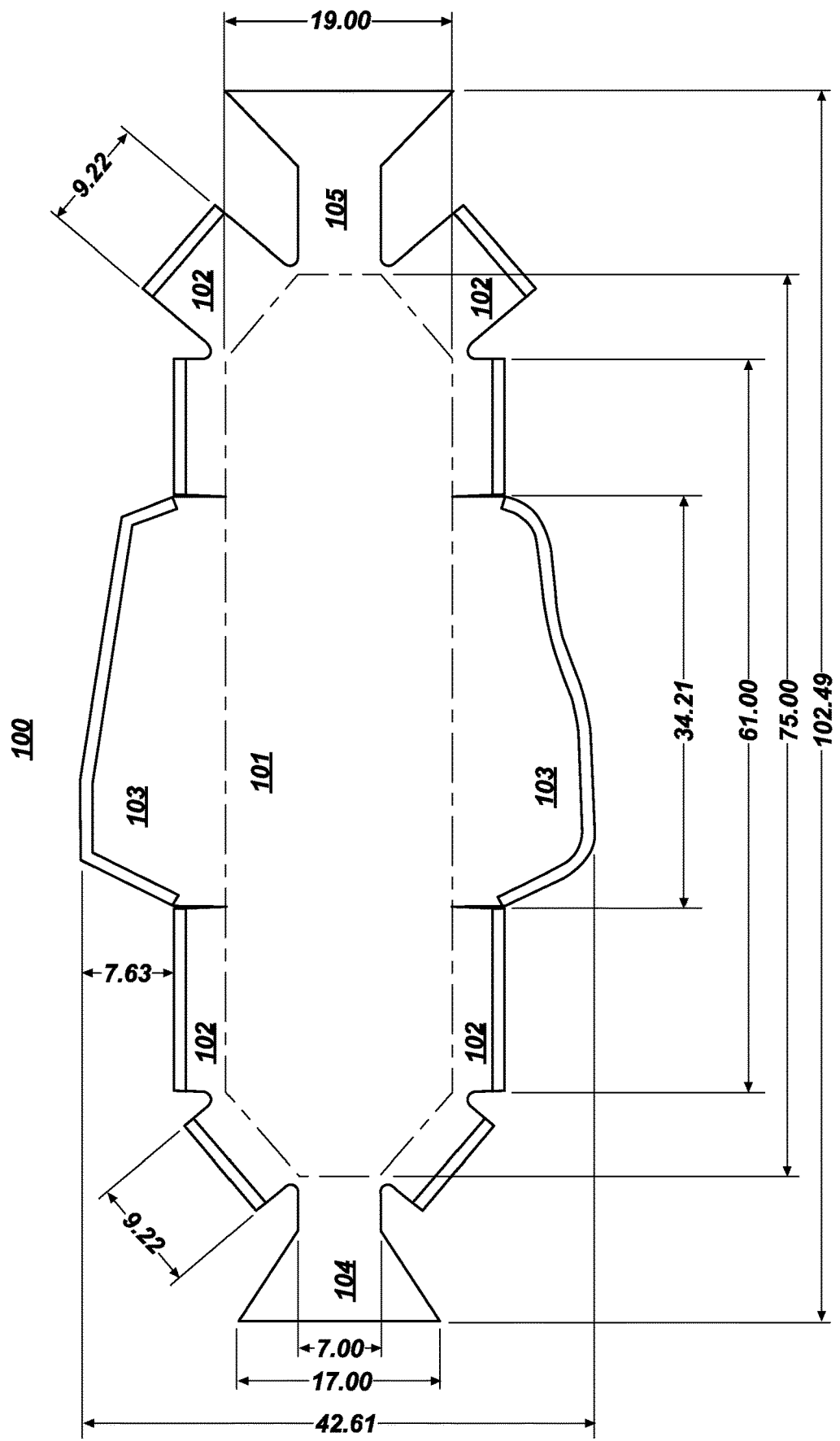
FIG. 1 is a view showing the shape of one embodiment of the device wherein the shape allows it to be fitted particularly to a patient transport device.

For the purposes of promoting an understanding of the principles in accordance with the present disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

In describing and claiming the present disclosure, the following terminology will be used in accordance with the definitions set out below. As used in this specification and the appended claims, the singular forms "a," "an," and "the" include plural referents unless the context clearly dictates otherwise. As used herein, the terms "comprising," "including," "having," "containing," "characterized by," and grammatical equivalents thereof are inclusive or open-ended terms that do not exclude additional, unrecited elements or method steps.

As used herein, the term "patient transport device" refers to any device used specifically to move a patient while allowing the patient to recline or lie down. This can include devices such as gurneys and stretchers used in vehicles such as ambulances, as well as devices such as mobile hospital beds which may be stationary for most of the time, but are designed to easily move.

Applicant has invented a protective cover for patient transport devices. Said cover is designed to act as a beneficial cover for a patient transport device, protecting the device itself and providing comfort and protection for the patient and benefitting the associated health care workers.

Figure 7:
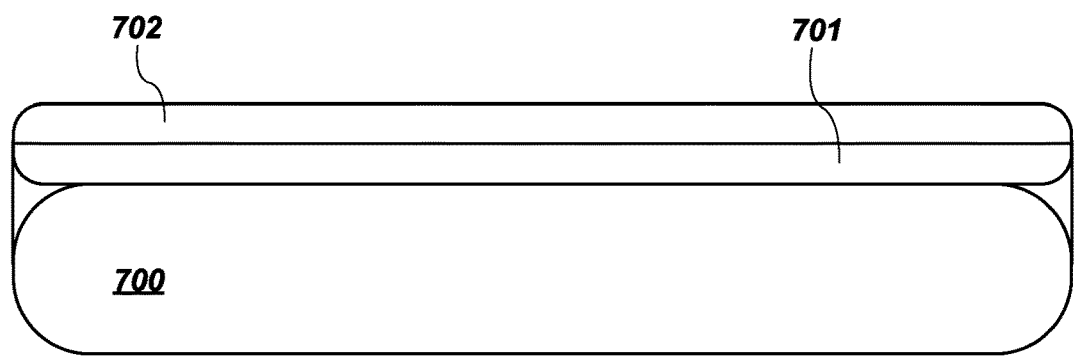
FIG. 7 shows the layers in one embodiment of the device, with an impermeable base layer and an absorbent top layer.

The protective cover is comprised of at least an impermeable base layer and an absorbent layer on top of the impermeable base layer, as diagrammatically shown in the cross sectional view of FIG. 7. The impermeable base layer 701 is form fitted to the patient transport device 700 and is impermeable to fluids. This layer 701 prevents fluids from contaminating the patient transport device and any pad attached to the device. The absorbent layer 702 is on top of the impermeable layer and is designed to trap and retain fluids. Thus in the case of a fluid contacting the protective cover, it is absorbed into the absorbent layer 702, and the impermeable layer 701 below prevents whatever is not absorbed from coming into contact with the patient transport device 700 and pad, as well as preventing whatever fluid is absorbed from draining or being pressed out of the absorbent layer 702 and contacting the patient transport device or pad. It should be noted that the width of the layers in FIG. 7 is not intended to limit the disclosure in any way. The width of the layers may need to be greater or lesser in proportion to the other layer in order to properly perform its function.

In one embodiment of the present disclosure 100, shown in FIG. 1, the protective cover may be shaped so as to precisely fit on a variety of patient transport devices, including different gurneys or stretchers. One exemplary patient transport device is shown by the outline 101 represented in FIG. 1. It will be appreciated that the dimensions (inches) illustrated in FIG. 1 are merely exemplary of those dimensions adapted for the patient transport device 101 but using the disclosure provided herein many different embodiments can be arrived at for many different patient transport devices beyond the particular patent transport device 101 represented in FIG. 1.

As illustrated in FIG. 1, the cover is shaped so that it securely covers the top surface of the patient transport device fitting snugly over the patient transport device, with one or more extensions 102 fitting around the various handles and extensions which may be part of the patient transport device. These extensions 102 may include covers for the railings 103 as seen in the FIG. 1. In one embodiment, the railing cover 103 is an impermeable layer which extends to cover the railings all around the patient transport device. This creates an area between the railings and the mattress which catches fluids, preventing fluids from entering the areas between the mattress and the railing, and preventing the contamination of other parts of the patient transport device which the patient does not contact. One embodiment of the cover may include a head cover 104 and a foot cover 105 which are shaped to cover and go around the head and foot of the device, providing an impermeable protection to these areas which may not be flat and thus are not easily covered by a previously available protection device.

The cover 100 can be attached to the patient transport device by whatever method is appropriate. In one embodiment, the cover may have a stretchable, elastic portion at the edge of the cover which is meant to fit around the bottom of the gurney or stretcher and secure the cover to the stretcher. In another embodiment, the cover may be secured by straps which wrap around a gurney.

In addition, the cover is designed to be completely disposable, allowing a new, clean protective cover to be utilized with each patient or each time a new, clean protective cover is desired.

Figure 2:
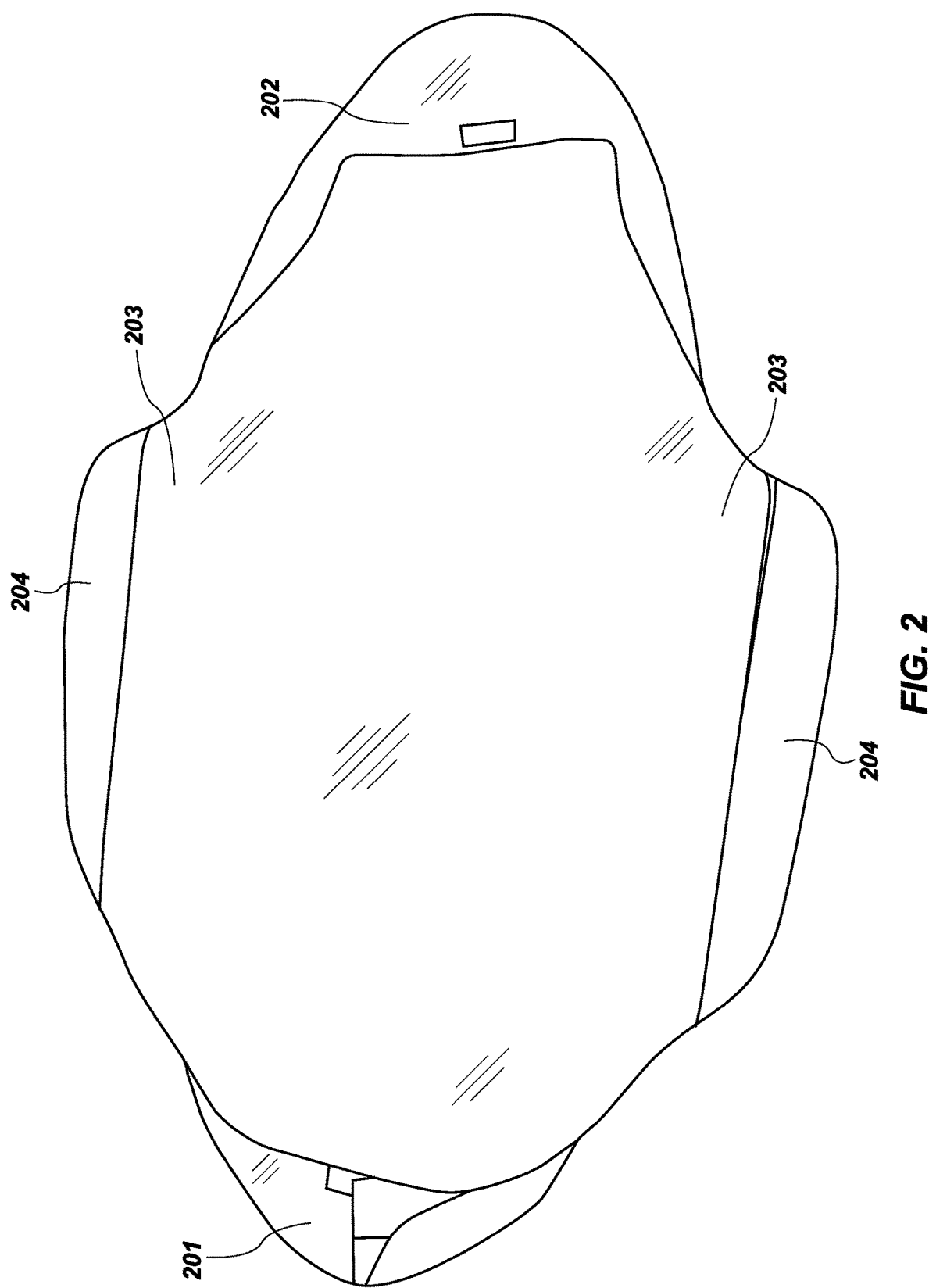
FIG. 2 shows another embodiment of the device showing the head and foot of an embodiment which secures the embodiment to the patient transport device as well as the railing covers.

FIG. 2 shows another embodiment of the present disclosure. In this embodiment a top or head portion 201 of the cover is designed to fit around the head or front portion of the gurney or stretcher. A lower portion of the cover 202 is designed to fit around the foot or lower portion of the gurney or stretcher 202. In addition, two wings 203 extend from the sides to fit on the railings of the gurney. The two wings each have a pocket 204 which tightly fits around the railing itself. It will be noted that other shapes may be necessary to precisely fit around a given configuration of a gurney or stretcher, but FIG. 2 shows one possible configuration which may well fit a number of different patient transport devices.

One embodiment of the protective cover has the above-mentioned characteristics and is designed to help transport patients for routine transports. Another embodiment is designed to be used for critical patient transports.

Figure 3:
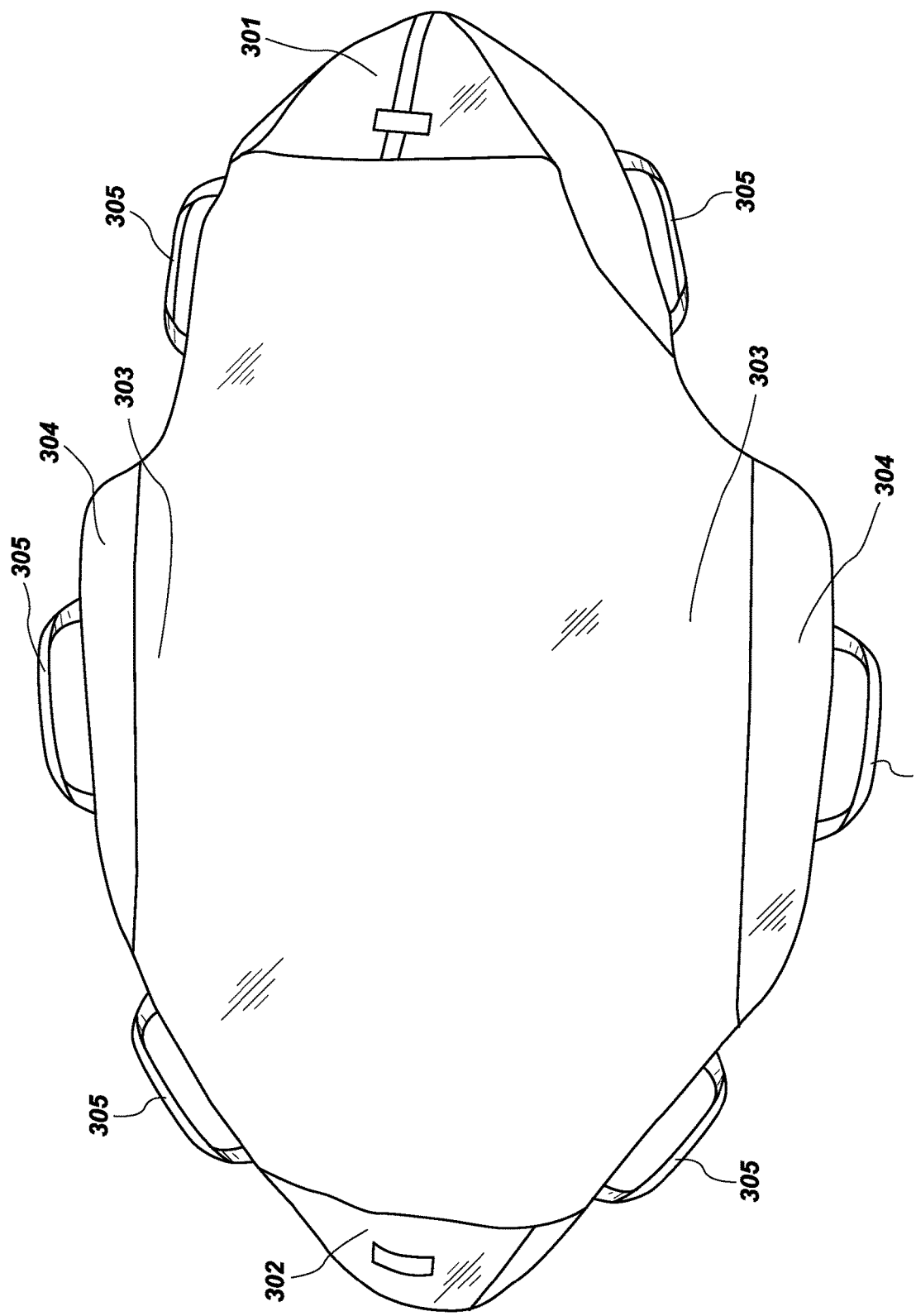
FIG. 3 shows one side of an embodiment of the device having handles to move a patient on the cover without the patient transport device.

In one embodiment of the invention shown in FIG. 3, the cover is designed with integrated lifting handles 305. The integrated handles 305 are built into the protective cover such that the protective cover can be used to transfer a patient from a patient transport device to a hospital bed or to a second patient transport device. In one embodiment there are six integrated lifting handles 305, but the number may change as may be required for effectiveness in moving a patient and for convenience in locating the handles along the device. It is to be understood that the embodiment represented in FIG. 3 provides merely on exemplary approach to providing integrated lifting handles. In this embodiment, the top or head portion 301 of the cover is designed to fit around the head of the patient transport device. A lower portion 302 of the cover is designed to fit around the foot portion of the patient transfer device. In addition, wings 303 and pockets 304 which secure a fit around the railings of a patient transfer device are present. In one embodiment there are six lifting handles 305 located on the sides of the cover, there being three lifting handles 305 on each side. In one embodiment these integrated lifting handles 305 are composed of fabric strong enough to hold the weight of the patient in the patient transfer device. In another embodiment the integrated lifting handles 305 may be composed of plastic or another material which can be disposed of with the cover.

Figure 4:
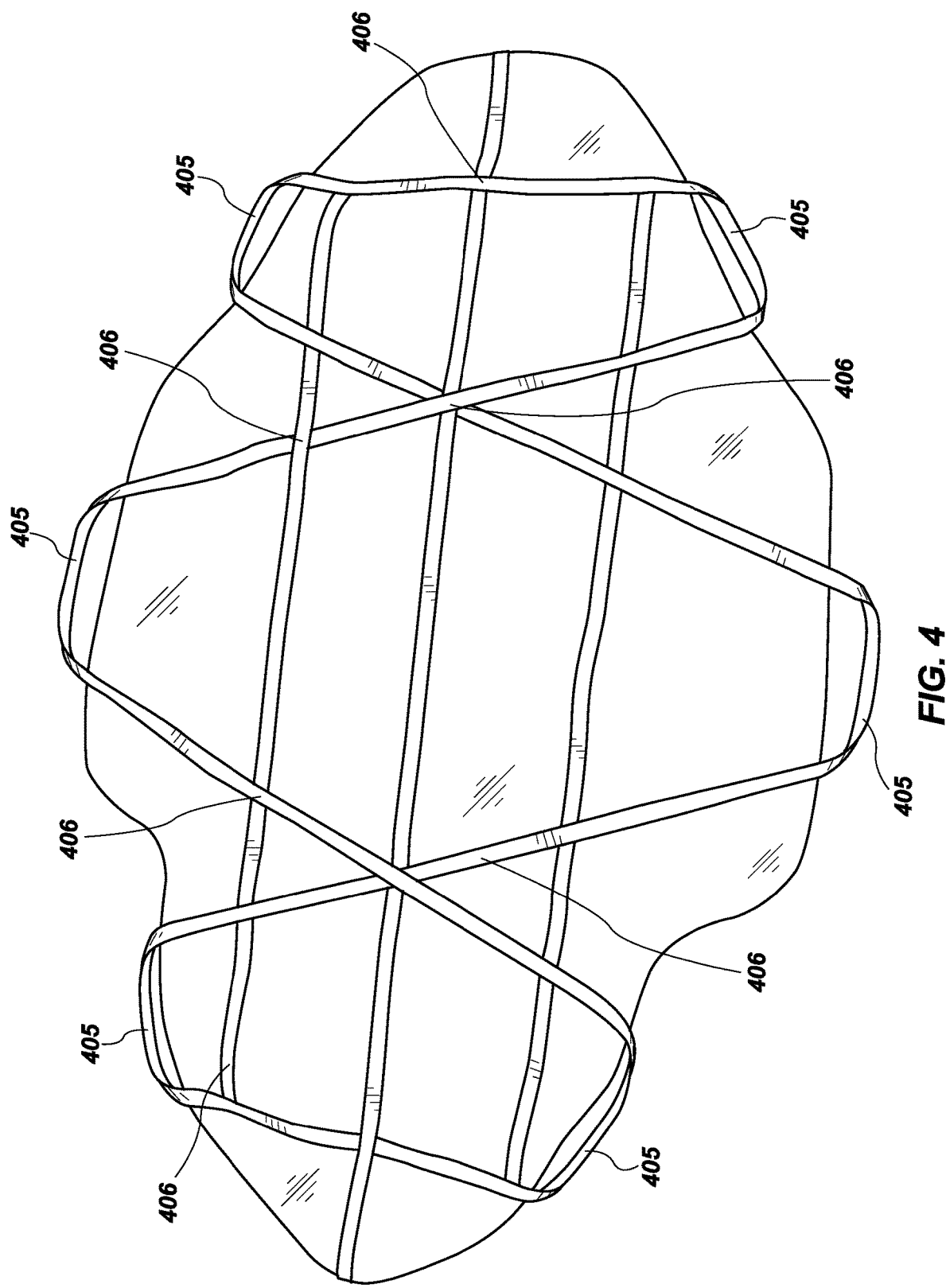
FIG. 4 shows the opposite side of a device having handles showing a web which supports the patient while being moved on the cover without a patient transport device.

One embodiment of a cover with integrated lifting handles is shown in FIG. 4. In one embodiment, the integrated lifting handles 405 connect to a support web 406 on the back of the device. The support web 406 is made out of any number of materials known to those skilled in the art which is strong enough to support a patient as the patient is lifted using the support handles. In one embodiment, the support web 406 is located on the bottom of the cover. In another embodiment, the support web 406 is located on what would be the top of the cover, and is formed of strong fabric connected to the integrated lifting handles 405. In yet another embodiment, the support web may be integrated into the interior of the fabrics used to construct the cover. In one embodiment of the cover, the support web 406 could be constructed from fabric straps. It should be noted that multiple arrangements of the support web are possible and those skilled in the art will appreciate what materials and structure should be adopted to be sufficient to support a patient as the patient is being lifted along with the protective cover. The support web 406 may be constructed out of a suitably strong fabric which is integrated with the cover. In other embodiments, the support web may be made out of another suitable material which can be attached to the surface of the cover or integrated within the cover. In one embodiment, the material of the cover itself may be strong enough to support a patient as the patient is lifted using the support handles, and the support handles are simply integrated with the material of the cover itself, while a support web is not needed.

Figure 5:
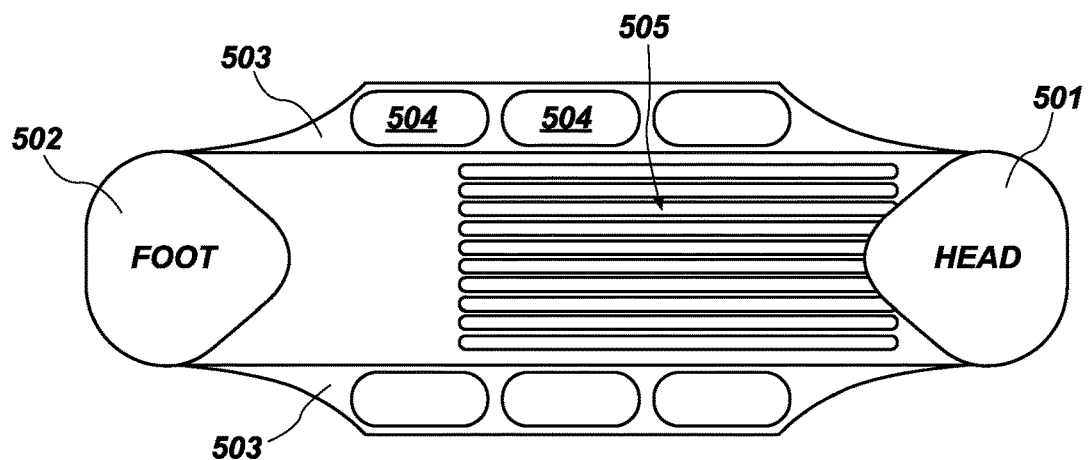
FIG. 5 shows one embodiment of the device showing the head and foot which secure it to the patient transport device as well as the railing covers and also shows the location of sleeves and pockets integrated into the absorbent layer which may contain heating or cooling elements.

In yet another embodiment, shown in FIG. 5, a top or head portion 501 of the cover is designed to fit around the head or front portion of the gurney or stretcher. A lower portion of the cover 502 is designed to fit around the foot or lower portion of the gurney or stretcher. In addition, two wings 503 extend from the sides to fit on the railings of the gurney. The two wings each have a pocket which tightly fits around the railing itself. In addition, the device comprises a series of pockets 504 sewn into the wings 503. In one embodiment these pockets 504 are located within an absorbent layer of the protective cover. These pockets 504 may contain a heating or cooling element. The cover may also comprise a series of sleeves 505 located in the main portion of the cover. These sleeves 505 may be sewn into the absorbent layer of the protective cover. These sleeves 505 may also contain a heating or cooling element.

In one embodiment, where at least one of the pockets 504 or sleeves 505 contains a heating element. This heating element may comprise any means for providing a steady warm temperature and increasing the temperature around it. In one embodiment, the heating element may be a chemical heating compound. In one embodiment, the heating element may produce sufficient heat to maintain or increase the patient's body temperature during transport. In one embodiment this may be accomplished by a chemical heating compound readily selected by those skilled in the art. In one embodiment, the chemical heating compound may be easily activated upon placing a new protective cover on the patient transport device. This may be accomplished by a compound which reacts to pressure or motion, or through a compound that reacts to exposure to the air by keeping the protective cover sealed before use. Any means known in the art for allowing a chemical heating compound to produce heat when needed may be used. The chemical heating compound may be sealed within the pockets 504 and sleeves 505 sewn within the absorbent layer of the cover.

In another embodiment, at least one of the pockets 504 or sleeves 505 may contain a cooling element. This cooling element may comprise any means for providing a steady cool temperature and reducing the temperature around it as can be selected by those skilled in the art and any structure providing the same function as the means for providing a steady cool temperature described herein is intended to fall within the scope of such structure. In one embodiment, the cooling element may be any material which maintains a low temperature, allowing the patient to be cooled if needed to maintain a proper body temperature during transport. In another embodiment this cooling may be accomplished by the use of other materials known in the art. In yet another embodiment, the pockets and sleeves may contain a cooling gel, which helps absorb heat from the patient being transported. In one embodiment, the cooling gel may help maintain the patient's temperature as needed during transport. The cooling gel may be sealed within the pockets 504 and sleeves 505 sewn within the absorbent layer of the cover.

It should be noted that in one embodiment, the pockets 504 and sleeves 505 seen in FIG. 5 are located within the absorbent layer of the cover and are not visible when looking at the cover itself. It should be further noted that the particular pattern of pockets and sleeves is not critical to the instant invention and any pattern which allows for a heating element and/or a cooling element to have sufficient contact with the patient to help maintain their temperature as needed is intended to be within the scope of this disclosure. It will also be noted that other shapes may be necessary to precisely fit around a given configuration of a gurney or stretcher, but the structure illustrated shows one possible configuration which may well fit a number of different patient transport devices.

In another embodiment, a reflective layer, which may be constructed of a reflective material such as Mylar®, may be integrated into the top layer of the cover. This reflective layer is integrated into the top layer of the cover to help patients in critical care situations retain body temperature.

Figure 6:
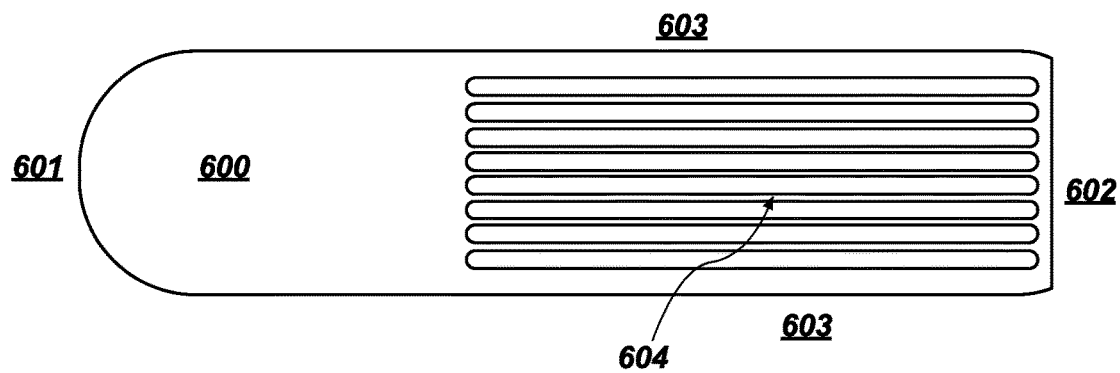
FIG. 6 shows one embodiment of a patient cover which is attaches to the foot of the device to cover the patient as required.

In one embodiment, another layer is attached to the protective cover at the foot of the cover, which is designed to pull up over the patient and enclose the patient, helping protect the patient and providing another barrier to contain fluids. This patient cover 600 is shown in FIG. 6. This patient cover 600 is attached at the foot 601, and may have a head portion 602 which does not secure to the protective cover and can be pulled up to cover the patient as needed. In one embodiment the sides 603 of the patient cover 600 may connect to the protective cover. In one embodiment this cover may have an absorbent layer on the inside, closest to the patient and an impermeable layer on the outside of the cover. This impermeable outer layer may help prevent contamination as with the impermeable layer on the protective cover over the patient transport device. This patient cover may also optionally include a reflective layer (as of Mylar® or other similar material) to help the patient retain body heat and maintain a consistent body temperature. In the current art a blanket or additional sheet is typically used to cover a patient.

In one embodiment the patient cover 600 may have a series of sleeves 604 sewn into the absorbent layer. One embodiment of the current disclosure incorporates an active heating element into the series of sleeves 604. This element may be a chemical heating pad integrated into the sleeves of the patient cover 600. This allows the patient cover 600 to provide additional warmth to the patient and help maintain body temperature. Another embodiment incorporates a cooling element into the sleeves 604 of the patient cover 600. This cooling element may be a chemical cooling pad integrated into the attached patient cover to help keep a patient cool. It may also comprise a cooling gel in the sleeves 604 of the patient cover 600. Those skilled in the relevant art will appreciate that other technologies can be implemented to provide heating and/or cooling structures.

An additional embodiment of the disclosure includes seat belt covers. These covers comprise a plastic cover that is integrated into the protective cover which extends out to surround the belt. The seat belt cover is integrated into the base layer of the gurney cover to prevent any fluids from contaminating the stretcher or seatbelt. The two ends of the seatbelt split the distal portion of the telescoping cover to connect without interference.

An additional embodiment of the invention is designed to cover the rear seat of a vehicle. This embodiment would be specifically designed for a police vehicle. Such an embodiment could be used to protect the interior of a police vehicle while transporting persons.

Accordingly, the exemplary embodiments of the present invention provide a novel protective cover for patient transport devices. It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A protective cover for patient transport devices, comprising:
   an impermeable base layer;
   an absorbent top layer;
   at least one railing cover designed to cover the railing of a patient transport device and provide a fluid catch area between a railing and mattress; and
   the protective cover is configured as a barrier over the entirety of a top area of a patient transport device to prevent a patient from directly contacting the patient transport device and to prevent a person rendering medical care from directly contacting the patient transport device.

2. The apparatus of claim 1, wherein the protective cover is disposable.

3. The apparatus of claim 1, wherein the protective cover incorporates at least one lifting handle designed to assist with transport of a patient by allowing the patient to be lifted on the protective cover and transferred between two patient transport devices.

4. The apparatus of claim 3, wherein the protective cover also comprises a support web which is configured to support a patient when the patient is being lifted on the protective cover, said support web being integral with the at least one lifting handle.

5. The apparatus of claim 1, also comprising a reflective layer which is configured to assist the patient in maintaining body temperature as the patient is transported.

6. The apparatus of claim 1, also comprising an attached patient cover, wherein the patient cover is attached to the protective cover at the foot and is capable of being pulled up over the patient and enclosing the patient.

7. The apparatus of claim 6 wherein the attached patient cover also comprises a reflective layer which is configured to assist the patient in maintaining body temperature as the patient is transported.

8. The apparatus of claim 6, wherein the attached patient cover comprises an impermeable layer which provides a barrier to contain fluids.

9. The apparatus of claim 6, wherein the attached patient cover also comprises an integrated chemical heating pad to affect the patient's temperature.

10. The apparatus of claim 6, wherein the attached patient cover also comprises an integrated chemical cooling pad to affect the patient's temperature.

11. The apparatus of claim 1, also comprising a seat belt cover, said cover being an integrated telescoping cover designed to surround a seat belt, preventing contamination.

12. The apparatus of claim 11, wherein the seat belt cover is integrated into the base layer of the protective cover.

13. The apparatus of claim 11, wherein the seatbelt splits the distal portion of the telescoping cover to connect without interference.

14. The apparatus of claim 1, also comprising an integrated heating element to affect the patient's temperature.

15. The apparatus of claim 14, wherein the integrated heating element is located within a series of pockets and sleeves integrated into the absorbent layer of the protective cover.

16. The apparatus of claim 14 wherein the integrated heating element comprises a series of pockets of chemical heating compound.

17. The apparatus of claim 1 also comprising an integrated cooling element to affect a patient's temperature.

18. The apparatus of claim 17 wherein the integrated cooling element is located within a series of pockets and sleeves integrated into the absorbent layer of the protective cover.

19. The apparatus of claim 17 wherein the integrated cooling element comprises a series of pockets of cooling gel.

20. The apparatus of claim 1 also comprising:
   At least one fitted head cover which is designed to fit over the head of a patient transport device and secure the protective cover to the patient transfer device;
   At least one fitted foot cover which is designed to fit over the foot of the patient transfer device and secure the protective cover to the patient transfer device; and,
   At least two wings which serve as extensions of the protective cover which fit up around a railing of the patient transfer device and serve as railing covers; wherein the railing cover is an integrated pocket designed to fit over the at least one railing of the patient transfer device.

21. A method of preventing contamination of a patient transport device, said method comprising providing a protective cover comprising at least:
   an impermeable base layer;
   an absorbent top layer;
   at least one fitted head cover which is designed to fit over the head of a patient transport device and secure the protective cover to the patient transfer device;
   at least one fitted foot cover which is designed to fit over the foot of the patient transfer device and secure the protective cover to the patient transfer device; and,
   at least two wings which serve as extensions of the protective cover,
   wherein the at least two wings also serve as railing covers which fit up around a railing of the patient transfer device and wherein the railing covers are integrated pockets designed to fit over the railing of the patient transfer device;
   wherein said protective cover is secured around the patient transport device and wherein the wings are secured around the railings of the patient transfer device.

22. The method of claim 21 also comprising moving a patient from the patient transport device to another location using the protective cover, wherein the protective cover incorporates at least one lifting handle designed to assist with transport of a patient by allowing the patient to be lifted on the protective cover and transferred between two locations.

23. The method of claim 21 also comprising providing means to aid a patient in maintaining body temperature.

24. The method of claim 23 wherein the means to aid a patient in maintaining body temperature comprises a reflective layer.

25. The method of claim 23 wherein the means to aid a patient in maintaining body temperature comprises an integrated heating element.

26. The method of claim 25 wherein the integrated heating element is located within a series of pockets and sleeves integrated into the absorbent layer of the protective cover.

27. The method of claim 25 wherein the integrated heating element comprises pockets of a chemical heating compound integrated into the absorbent layer of the protective cover.

28. The method of claim 23 wherein the means to aid a patient in maintaining body temperature comprises an integrated cooling element.

29. The method of claim 28 wherein the integrated cooling element is located within a series of pockets and sleeves integrated into the absorbent layer of the protective cover.

30. The method of claim 28 wherein the integrated cooling element comprises a series of pockets of cooling gel.

31. The method of claim 21 also comprising preventing contamination of a seat belt by providing a seat belt cover, said cover being an integrated telescoping cover designed to surround a seat belt, preventing contamination.

32. The method of claim 31 also comprising allowing the seatbelt to connect without interference by providing a cover such that the seatbelt splits the distal portion of the telescoping cover to connect without interference.

33. The method of claim 31 wherein the seat belt cover is integrated into the base layer of the protective cover.

34. A protective cover for patient transport devices, comprising:
   At least one fitted head cover which is designed to fit over the head of a patient transport device and secure the protective cover to the patient transfer device;
   At least one fitted foot cover which is designed to fit over the foot of the patient transfer device and secure the protective cover to the patient transfer device; and,
   At least two wings which serve as extensions of the protective cover;
   Wherein the two wings also serve as railing covers which fit up around one or more railings of the patient transfer device and wherein the railing covers are integrated pockets designed to fit over the railing of the patient transfer device.

35. The apparatus of claim 34 also comprising:
   an impermeable base layer;
   an absorbent top layer.

36. The apparatus of claim 34 wherein the protective cover is disposable.

37. The apparatus of claim 34 also comprising at least one lifting handle designed to assist with transport of a patient by allowing the patient to be lifted on the protective cover and transferred between two patient transport devices.

38. The apparatus of claim 37 wherein the protective cover also comprises a support web which is configured to support a patient when the patient is being lifted on the protective cover, said support web being integral with the at least one lifting handle.

39. The apparatus of claim 34 also comprising an attached patient cover, wherein the patient cover is attached to the protective cover at the foot and is capable of being pulled up over the patient and enclosing the patient.

40. The apparatus of claim 39 wherein the attached patient cover also comprises a reflective layer which is configured to assist the patient in maintaining body temperature as the patient is transported.

41. The apparatus of claim 39 wherein the attached patient cover comprises an absorbent lower layer and an impermeable upper layer.

42. The apparatus of claim 41 wherein the attached patient cover also comprises an integrated heating element to help control the patient's temperature.

43. The apparatus of claim 42 wherein the integrated heating element in the attached patient cover is located within a series of pockets and sleeves integrated into the absorbent layer of the attached patient cover.

44. The apparatus of claim 42 wherein the integrated heating element comprises pockets of a chemical heating compound integrated into the absorbent layer of the attached patient cover.

45. The apparatus of claim 41 wherein the attached patient cover also comprises an integrated cooling element to help control the patient's temperature.

46. The apparatus of claim 45 wherein the integrated cooling element in the attached patient cover is located within a series of pockets and sleeves integrated into the absorbent layer of the attached patient cover.

47. The apparatus of claim 45 wherein the integrated cooling element comprises pockets of a cooling gel integrated into the absorbent layer of the attached patient cover.

48. The apparatus of claim 34, wherein the protective cover also comprises an integrated chemical heating pad to help control the patient's temperature.

49. The apparatus of claim 34, wherein the protective cover also comprises an integrated chemical cooling pad to help control the patient's temperature.

50. Apparatus of claim 34 also comprising a seat belt cover, said cover being an integrated telescoping cover designed to surround a seat belt, preventing contamination.

51. The apparatus of claim 50 wherein the seat belt cover is integrated into the base layer of the protective cover.

52. The apparatus of claim 50 wherein the seatbelt splits the distal portion of the telescoping cover to connect without interference.

* * * * *